(12) United States Patent
Westcott

(10) Patent No.: US 8,591,482 B2
(45) Date of Patent: Nov. 26, 2013

(54) HUBER NEEDLE SAFETY APPARATUS

(76) Inventor: Mark Westcott, New York, NY (US)

(*) Notice: Subject to any disclaimer, the term of this patent is extended or adjusted under 35 U.S.C. 154(b) by 0 days.

(21) Appl. No.: 13/406,558

(22) Filed: Feb. 28, 2012

(65) Prior Publication Data

US 2013/0226101 A1    Aug. 29, 2013

(51) Int. Cl.
*A61M 5/00* (2006.01)
*A61M 5/32* (2006.01)

(52) U.S. Cl.
USPC ............ 604/273; 604/272; 604/263; 604/162

(58) Field of Classification Search
USPC .......... 604/263–264, 273–274, 162, 268, 272
See application file for complete search history.

(56) References Cited

U.S. PATENT DOCUMENTS

| 2006/0030825 A1* | 2/2006 | Enns et al. ..................... 604/264 |
| 2007/0078432 A1* | 4/2007 | Halseth et al. ................ 604/500 |

* cited by examiner

*Primary Examiner* — Manuel Mendez
*Assistant Examiner* — Rebecca E Eisenberg

(57) ABSTRACT

The invention presented is a needle system to access a subcutaneous port primarily for the administration of chemotherapy, designed to protect the health care worker from inadvertent needle injury by isolation of the needle tip within base and tower components. A rotating collar is designed to keep the needle immobile until access of the port is desired when it can be rotated to align a cut out with a corresponding cut out of the tower that houses the needle for advancement of the needle downward into the port. On retraction, the collar can be rotated, locking the needle back into a retracted position within the tower.

13 Claims, 7 Drawing Sheets

HUBER NEEDLE SAFETY APPARATUS

FIELD OF THE INVENTION

The present invention relates in general to Huber needles, and more specifically to a safety mechanism for protecting health care workers from inadvertent needle injury during access of subcutaneous ports.

BACKGROUND OF THE INVENTION

Subcutaneous ports for the administration of chemotherapy were a significant medical advancement. They are placed in numerous cancer patients every year and are accessed several times per month in many patients. Placement involves a surgical procedure wherein the catheter is placed most commonly into the jugular or subclavian vein and its attached port implanted subcutaneously over the upper chest. Because they are subcutaneous ports are associated with a lower rate of infection compared with intravenous catheter systems which exit the skin such as hickman catheters, triple lumen catheters and peripherally inserted central catheters. Non-coring needles are required to access subcutaneous chemotherapy ports (infusaports) to ensure the septum of the device is not damaged as would occur with a standard beveled needle.

The tip of a Huber needle, which has a reversed bevel design, is very sharp and exposes the clinician to needle stick injuries. These injuries can occur immediately after the needle is removed from its packaging due to its exposed tip in many designs, during insertion into the port and during needle removal from the port. In particular, the removal of Huber needles requires the use of the non-dominant hand of the clinician to stabilize the implanted port, while the needle is withdrawn from the septum. Rebound injuries are common with Huber needles due to the unusual force required to overcome the resistance of the elastic septum. When the resistance is overcome the needle quickly exits the skin and then commonly advances back towards the stabilizing hand resulting in needle puncture of the clinician's finger(s). This rebound effect accounts for a majority of Huber needle stick injuries. The placement and removal of these non-coring needles poses considerable risk to the health care provider due to:

1. the need to locate by palpation and then stabilize the port with the fingers of one hand while introducing the non-coring needle with the opposite hand between the stabilizing finger and
2. the considerable force required to pass the needle through the septum into the port chamber as well as during retraction of the needle from the device.

Due to the prevalence of blood borne illnesses including Acquired Immunodeficiency Syndrome (AIDS) and hepatitis B and C the risk of contracting a serious illness during the access of subcutaneous ports is of great concern to many health care workers. Inadvertent needle injuries to health care providers are a known risk during access of subcutaneous ports with many of the available needle access systems. The needle system presented herein allows for safe access of subcutaneous ports with little or no risk of inadvertent needle injury to the health care provider.

A subcutaneous port system consists of two parts, a catheter placed into a vein which is connected to a port which is a centrally hollow device. The centrally hollow portion of the port and lumen of the catheter are contiguous. When a needle is placed through the septum of a port into its hollow center, blood can be removed for analysis and medications can be administered directly through the catheter attached to the port into the blood stream. The needles used to penetrate the septum must be of the non-coring variety.

SUMMARY OF THE INVENTION

The present invention overcomes the disadvantages and shortcomings of the problems of the prior art by allowing for safe access of subcutaneous ports with little or no risk of inadvertent needle injury to the health care provider. This novel non-coring needle system consists of a base/tower, rotating collar and non-coring needle that is designed such that the tip of the needle cannot come in contact with the operator prior to insertion, during access of the port, or following its removal. Its simple design allows for easy manufacturing and reduced cost.

In a preferred version of the present invention, the system is comprised of a base, a rotatable collar, and a non-coring needle. The base/tower consists of a round cupped base from the center of which the tower arises which houses the non-coring needle. Holes in the base allow for the escape of moisture from the skin while the port is accessed. The round base is placed over the port which allows for centering of the needle system over the port septum. The fingers of one hand can be placed on the base around the tower, holding it in place over the port. Since the needle is within the centrally located tower there is no possibility of injury to the fingers stabilizing the base. The tower extends through the base so that when the base is placed on the skin overlying the port the needle will be centered over the septum. This is also a safety feature since the needle is not exposed prior to access or following removal as it is contained within the tower. A notch in the tower which extends from its top to the base allows needle movement downward into the port when lined up with the notch in the collar.

The rotating collar is preferably affixed to and surrounds the tower of the base. A notch of the same width as the notch on the tower is located on the opposite side of the notch on the tower when the needle system is removed from the sterile packaging. With the notches in such an orientation the needle cannot move downward through the notch in the tower. After the base is placed over the port and stabilized with the fingers of one hand, the collar is rotated 180 degrees with the fingers of the other hand such that the notches line up. With the notches aligned the non-coring needle can then be pushed downward through the tower notch through the port septum. When the needle is to be removed, the base is again stabilized against the port and the needle pulled upward through the notch. The collar is then turned 180 degrees so that the notches are no longer aligned, holding the needle in its original position.

The non-coring needle is housed within the base tower. A handle extends perpendicular to the needle shaft. This handle is grasped during needle insertion and removal. A flange where the handle meets the needle keeps the needle from being pulled upward out of the tower.

SUMMARY OF THE INVENTION

The present invention overcomes the disadvantages and shortcomings of the problems of the prior art by allowing for safe access of subcutaneous ports with little or no risk of inadvertent needle injury to the health care provider. This novel non-coring needle system consists of a base/tower, rotating collar and non-coring needle that is designed such that the tip of the needle cannot come in contact with the operator prior to insertion, during access of the port, or following its removal. Its simple design allows for easy manufacturing.

In a preferred version of the present invention, the system is comprised of a base, a rotatable collar, and a non-coring needle. The base/tower consists of a round cupped base from the center of which the tower arises which houses the non-coring needle. Holes in the base allow for the escape of moisture from the skin while the port is accessed. The round base is placed over the port which allows for centering of the needle system over the port septum. The fingers of one hand can be placed on the base around the tower, holding it in place over the port. Since the needle is within the centrally located tower there is no possibility of injury to the fingers stabilizing the base. The tower extends through the base so that when the base is placed on the skin overlying the port the needle will be centered over the septum. This is also a safety feature since the needle is not exposed prior to access or following removal as it is contained within the tower. A notch in the tower which extends from its top to the base allows needle movement downward into the port when lined up with the notch in the collar.

The rotating collar is preferably affixed to and surrounds the tower of the base. A notch of the same width as the notch on the tower is located on the opposite side of the notch on the tower when the needle system is removed from the sterile packaging. With the notches in such an orientation the needle cannot move downward through the notch in the tower. After the base is placed over the port and stabilized with the fingers of one hand, the collar is rotated 180 degrees with the fingers of the other hand such that the notches line up. With the notches aligned the non-coring needle can then be pushed downward through the tower notch through the port septum. When the needle is to be removed, the base is again stabilized against the port and the needle pulled upward through the notch. The collar is then turned 180 degrees so that the notches are no longer aligned, holding the needle in its original position.

The non-coring needle is housed within the base tower. A handle extends perpendicular to the needle shaft. This handle is grasped during needle insertion and removal. A flange where the handle meets the needle keeps the needle from being pulled upward out of the tower.

BRIEF DESCRIPTION OF THE DRAWINGS

For a more complete understanding of the present invention, reference is made to the following detailed description of the exemplary embodiment(s) considered in conjunction with the accompanying drawing in which.

DETAILED DESCRIPTION OF THE EXEMPLARY EMBODIMENTS

Figure 1:
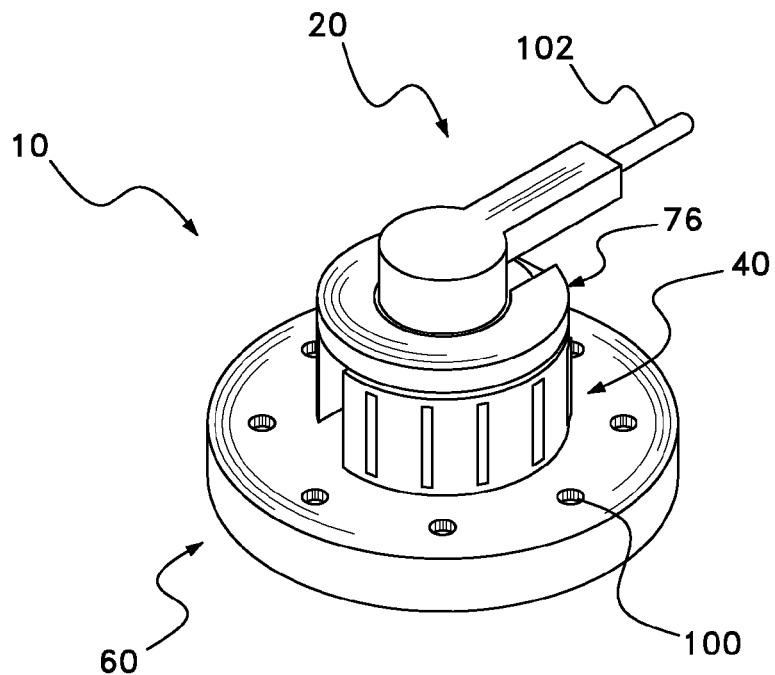
FIG. 1 is a perspective view of the Huber Needle Safety Apparatus.
Figure 2:
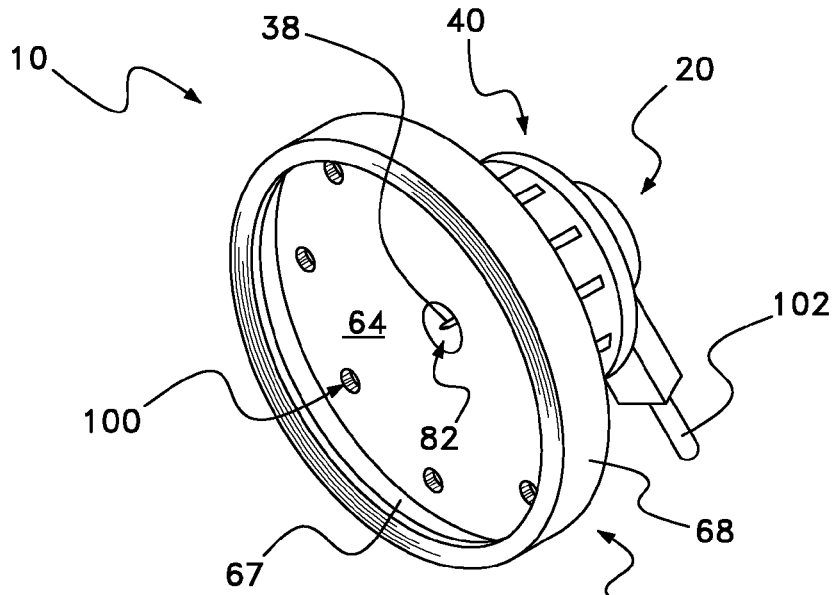
FIG. 2 is a perspective view of the Huber Needle Safety Apparatus of FIG. 1 showing the bottom.
Figure 3:
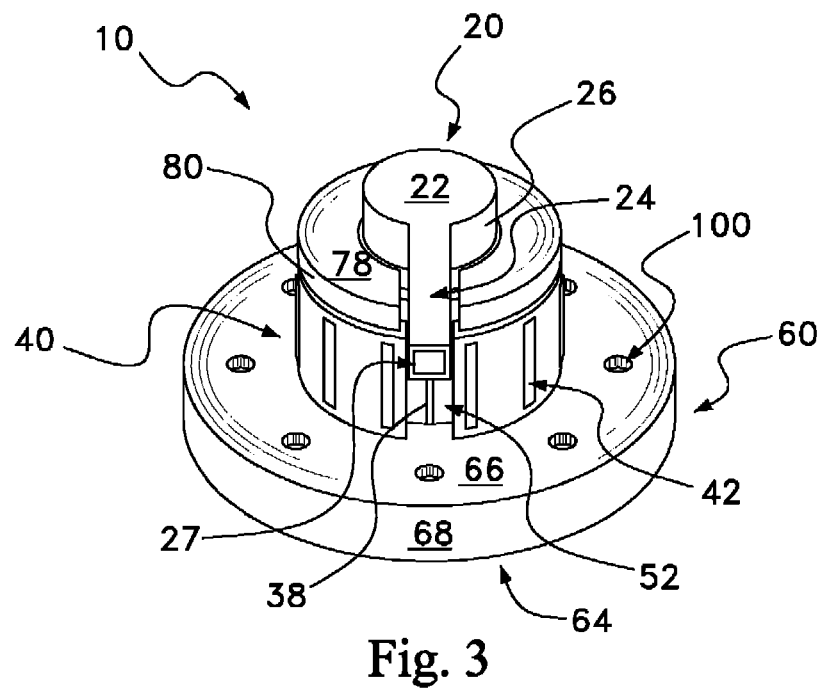
FIG. 3 is a perspective view of the Huber Needle Safety Apparatus of FIG. 1 show from FIG. 4 is a perspective view of the Huber Needle Safety Apparatus of FIG. 1 shown from the front without the tubing inserted after needle deployment.
Figure 4:
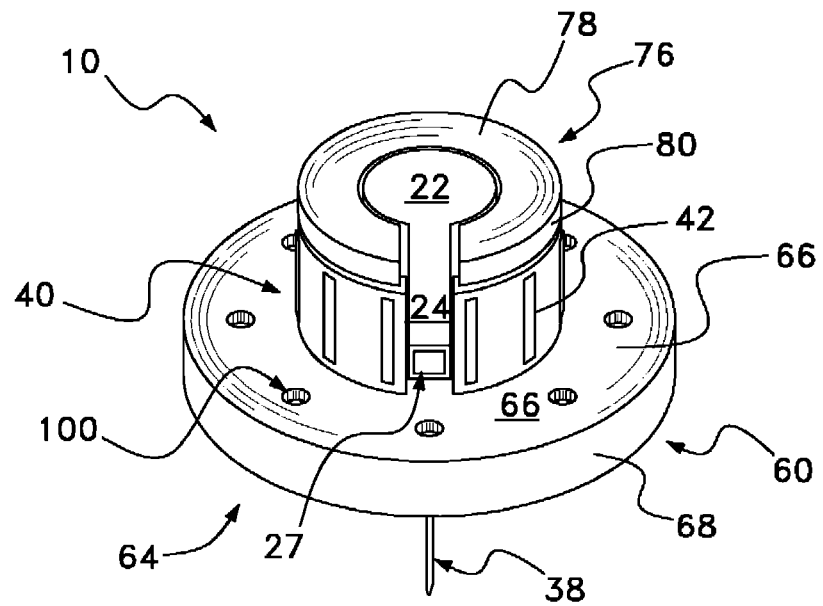
Figure 5:
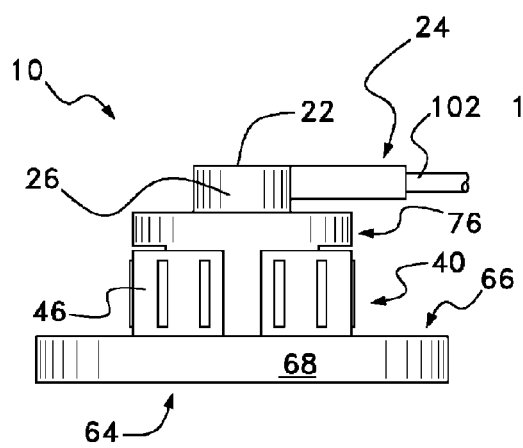
FIG. 5 is a left side elevational view of the Huber Needle Safety Apparatus of FIG. 1.
Figure 6:
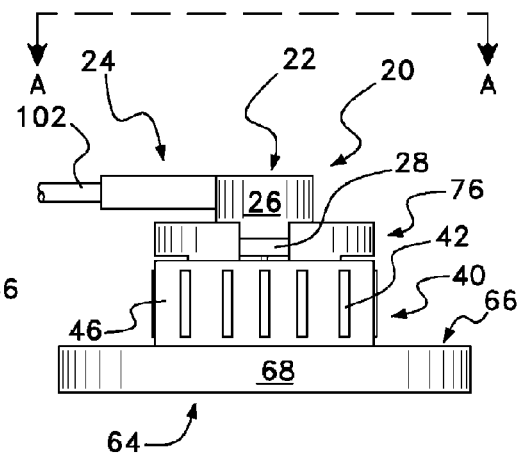
FIG. 6 is a right side elevational view of the Huber Needle Safety Apparatus of FIG. 1.
Figure 7:
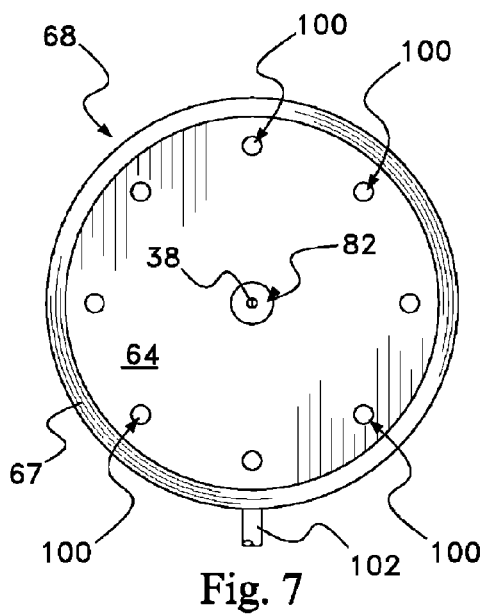
FIG. 7 is a bottom plan view of the Huber Needle Safety Apparatus of FIG. 1.
Figure 8:
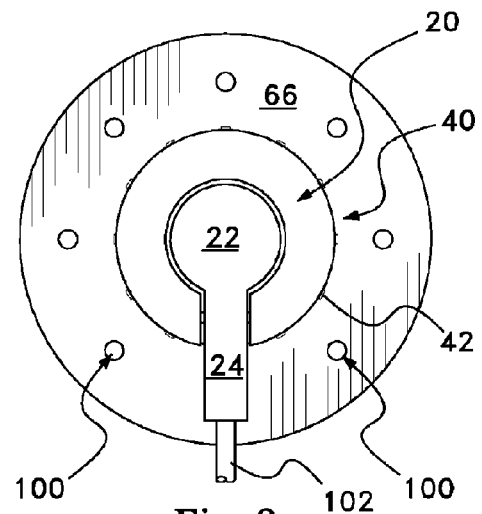
FIG. 8 is a top plan view of the Huber Needle Safety Apparatus of FIG. 1.

Referring to FIGS. 1-19, a Huber needle safety apparatus 10, constructed in accordance with the present invention, is shown to include a non-coring needle assembly 20, a collar, 40, and a base 60, that allows for zero exposure of the needle 38 to a care service provider because the tip of the needle 38 is disposed fully within the cavity 72 of the base tower 70 prior to deployment and upon removal from a subcutaneous port of a patient. FIGS. 3-4 illustrate the Huber needle safety apparatus 10 in a pre-deployed and a deployed position respectively.

As shown more clearly in FIGS. 9-12, the base 60 includes a bottom 62 at a first distal end that is designed and configured to matingly engage with a subcutaneous port embedded in a patient. The base bottom 62 is substantially circular in cross section and includes a bottom surface 64 and a base lip 67 that together provide a recessed area designed to matingly slide over and on top of the port. The base bottom 62 includes side wall 68 and a top surface 66 designed with annular ventilation holes 100 that are disposed at regular intervals circumferentially along the base top surface 66 and which pass through to the bottom surface 64 allowing for venting of humidity that may build when the Huber needle safety apparatus 10 is in place with a port.

Still referring to FIGS. 9-12, the base further includes a base tower 70 that extends upwardly and substantially perpendicularly from the base bottom 62, and also includes a base top 76 at a second distal end. The base top 76 is substantially C-shaped, and includes an outer wall 80, an inner wall 110, opposite the outer wall 80, and a top surface 78. The outer wall 80 and inner wall 110 form the upper opening of the annular cavity 82 of the tower 70. Both outer wall 80 and inner wall 110 are recessed from the top surface 78 of the base top 76 such that the top 76 extends past and perpendicularly to the outer wall 80 of the tower 70 and also extends over the inner wall 110. A cut out 75 is formed to pass through the tower 70 and the top surface 76 through which the needle assembly 20 may pass for deployment or retraction. The cut out 75 is substantially perpendicular to the base top 76 and extends along the base tower 70 longitudinal axis.

Referring to FIGS. 1-6 and 16-19, the Huber needle safety apparatus 10 includes a needle assembly 20 and a tube 102 for delivery of medication through the needle 38. The needle assembly 20 is comprised of a housing and a beveled tip, non-coring needle 38 in a 90 degree configuration typical of the non-coring needles used in the medical profession. The housing of the needle assembly 20 is formed from an annular cap 22, a depressor handle 24, and a retaining lip 36 formed beneath the annular cap 22 with a diameter greater than that of the annual cap 22. The retaining lip 24 has a bottom surface 21 with an annular aperture 23 through which the needle 38 passes. The depressor handle 24 is substantially rectangular in cross section and extends outwardly from the needle assembly cap 22. The depressor handle 24 is designed to include a hollow channel 27 though which tubing 102 passes to slidingly engage with the needle 38 within the channel 27. Retaining nubs 39 unitarily formed on the distal, blunt end of needle 38 allow for frictional retaining of the tubing 102 onto the needle 38.

Figure 9:
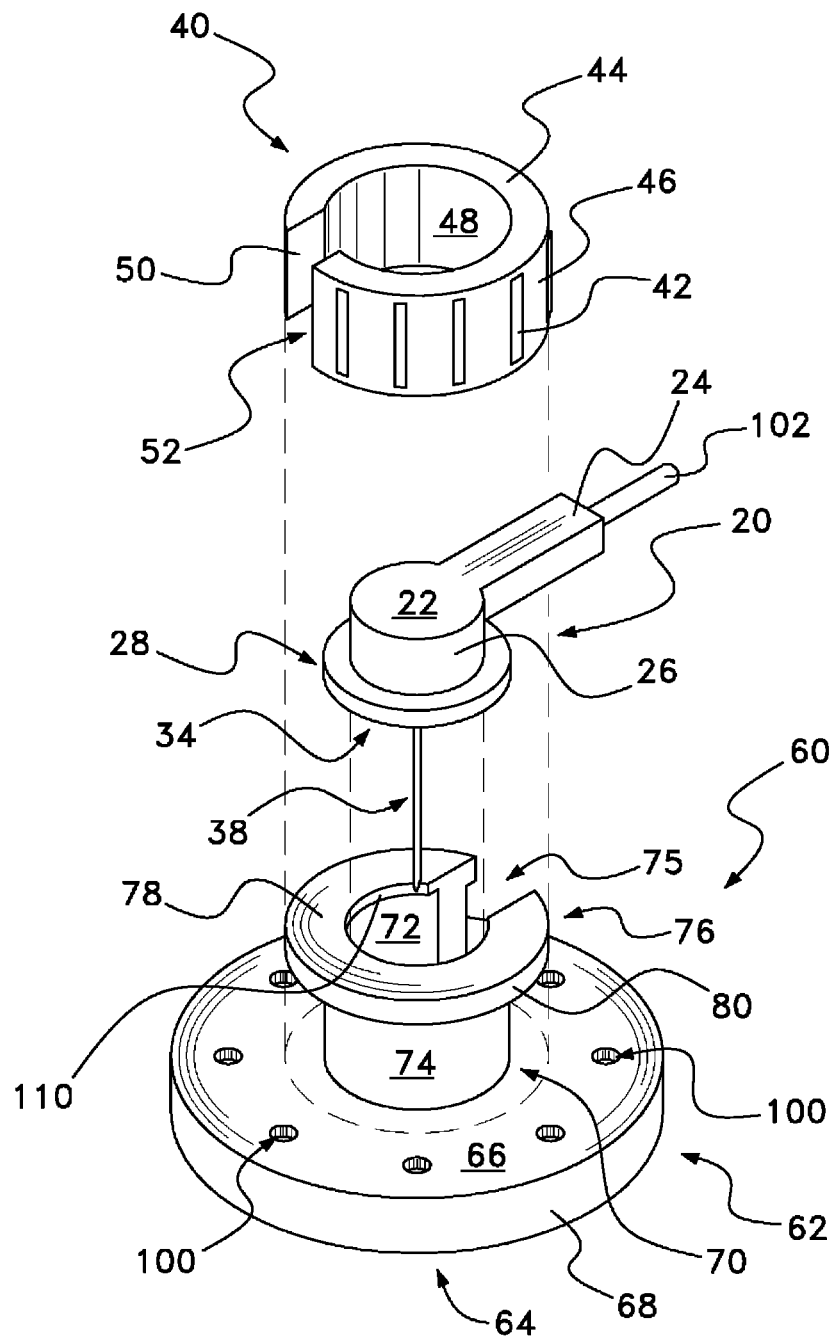
FIG. 9 is an exploded perspective view of the Huber Needle Safety Apparatus of FIG. 1.
Figure 10:
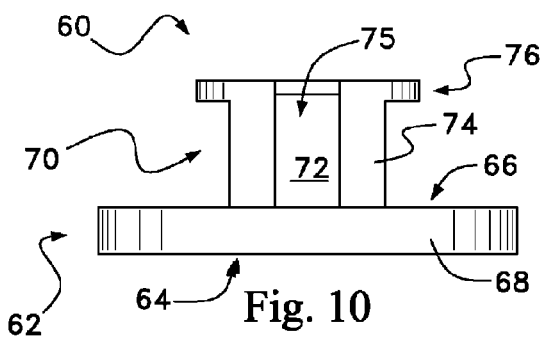
FIG. 10 is a front elevational view of the base of the Huber Needle Safety Apparatus of FIG. 1.
Figure 16:
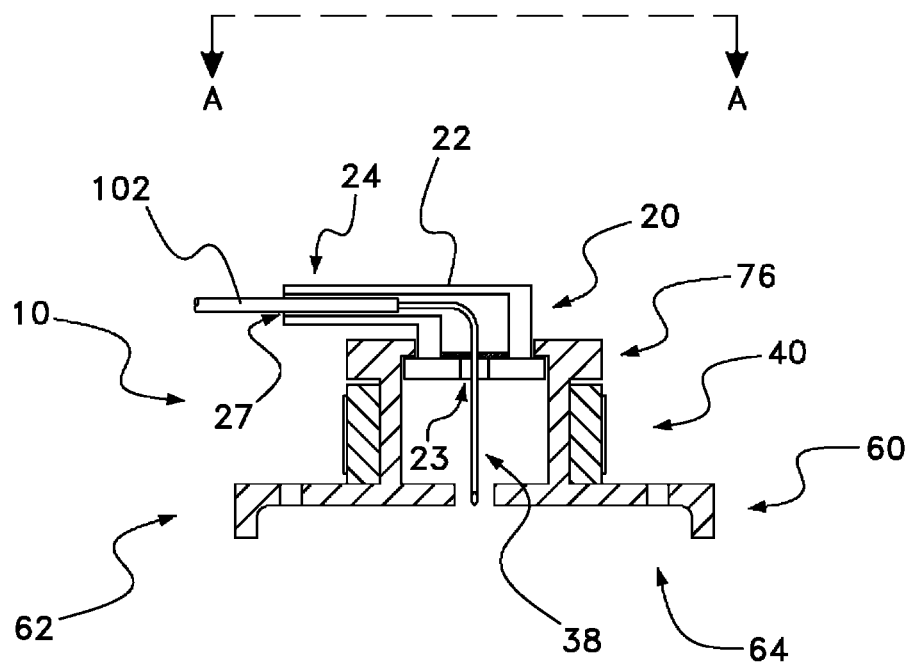
FIG. 16 is a left side elevational cross sectional view taken through line A-A of the Huber Needle Safety Apparatus of FIG. 6.
Figure 17:
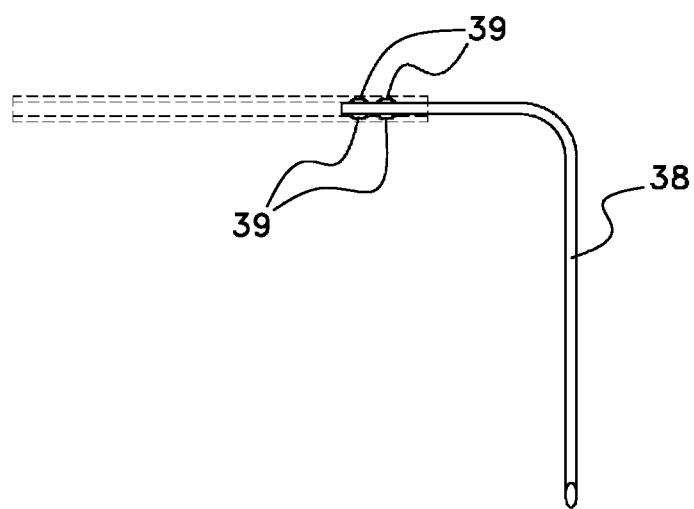
FIG. 17 is a left side elevational view of the non-coring needle of the Huber Needle Safety Apparatus of FIG. 1 shown with the tubing in dotted lines.
Figure 18:
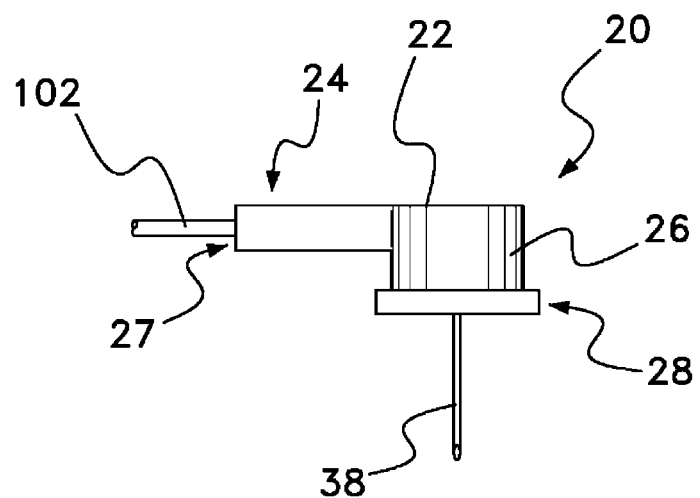
FIG. 18 is a left side elevational view of the needle assembly of the Huber Needle Safety Apparatus of FIG. 1.
Figure 19:
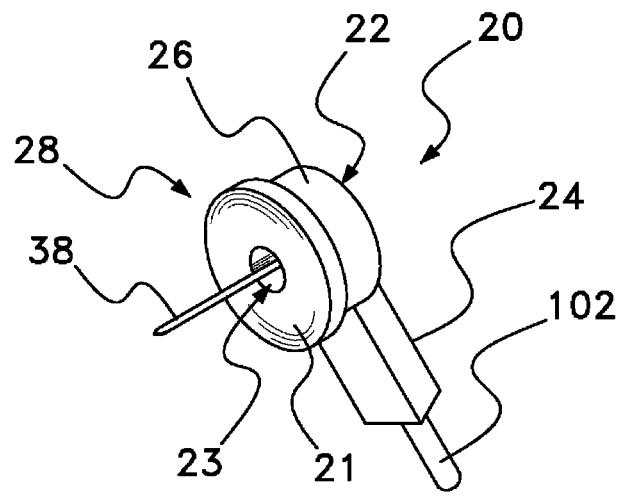
FIG. 19 is a bottom perspective view of the needle assembly of the Huber Needle Safety Apparatus of FIG. 1.

Now referring to FIGS. 9 and 16, the needle assembly 20 is constructed so that the retaining lip 36 can be slidingly placed within the tower base cavity and substantially under the overlapping top surface 76 of the base 60 for assembly. The collar 40 can then be releasably snapped into place around the base tower 70 such that the inner wall 48 of the collar 40 is disposed adjacently to the outer wall 74 of the base tower 70, and over the base cut out 75, for locking of the needle assembly 20 in a static position.

Figure 13:
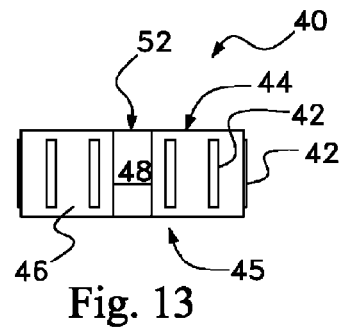
FIG. 13 is a front elevational view of the collar of the Huber Needle Safety Apparatus of FIG. 1.
Figure 11:
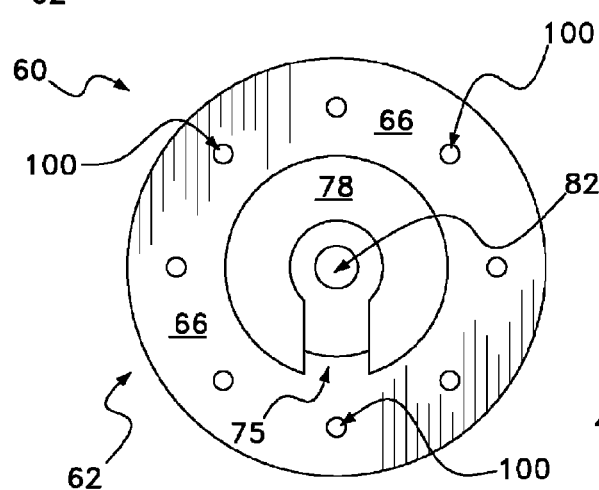
FIG. 11 is a top plan view of the base of the Huber Needle Safety Apparatus of FIG. 1.
Figure 14:
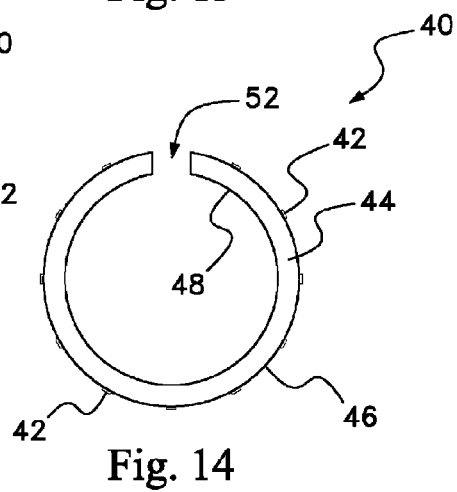
FIG. 14 is a top plan view of the collar of the Huber Needle Safety Apparatus of FIG. 1.
Figure 12:
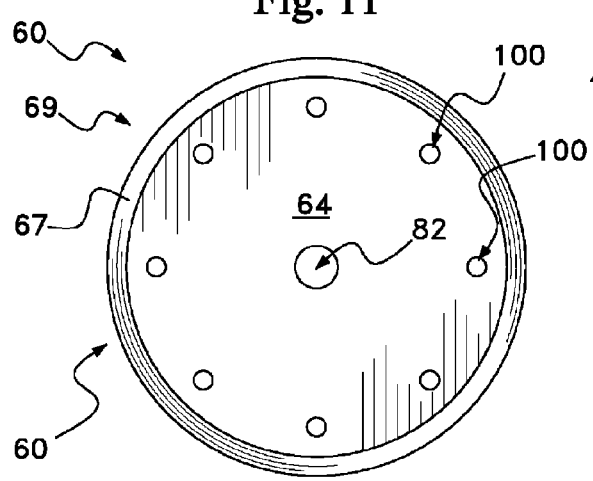
FIG. 12 is a bottom plan view of the base of the Huber Needle Safety Apparatus of FIG. 1.
Figure 15:
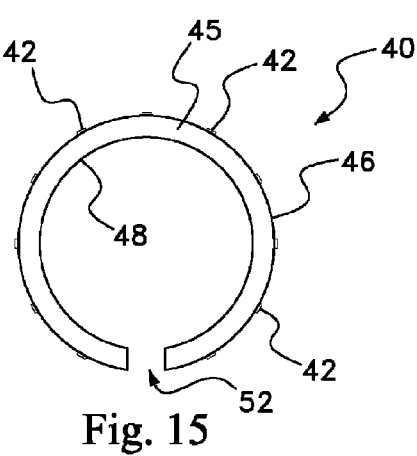
FIG. 15 is a bottom plan view of the base of the Huber Needle Safety Apparatus of FIG. 1.

Referring to FIGS. 13-15, the collar 40 is designed and configured to matingly engage with the tower 70 of the base 60. The collar 40 is substantially C-shaped, forming an inner cavity, with an upper surface 44, a lower surface 45 opposite the upper surface, an outer wall 46 and an inner wall 48, in which the C-shape is formed when the outer wall 46 and inner wall 48 terminate at cut out surfaces 50. Collar grips 42 are disposed at regular intervals circumferentially around the outer wall 46. The collar grips 42 provide a non-slipping means for the caregiver to rotate the collar 40 around the base tower 70 for alignment of the cutouts and deployment of the needle assembly 20. The collar 40 includes a collar cut out 52 that is used to lock the needle assembly 20 in place either prior to deployment or after retraction.

Now referring to FIGS. 3-6, when the caregiver is ready to insert the needle 38 into a port, the collar 40 is rotated around the base tower 70 such that the collar cut out 52 is aligned with the tower cut out 75. The caregiver then can easily exert downward force onto the depressor tab 24 of the needle assembly 20 until the tip of the needle 38 enters the port. The caregiver can then rotate the collar 40 to a position such that the collar cut out 52 is no longer in alignment with tower cut out 75, and effectively locks the needle assembly 20 in place. For retraction of the needle 38 from the port, this process is essentially reversed.

While there has been described the preferred embodiment of this invention, it will be obvious to those skilled in the art that various other embodiments, changes, equivalents, and modifications may be made therein without departing from the spirit of scope of this invention. It is therefore aimed to cover all such changes, equivalents, and modifications as fall within the spirit and scope of the invention. For example, different kinds of devices could be used to attach the tube to the non-coring needle.

The invention is not limited in its application to the details of construction and to the arrangements of the components set forth in the description above or illustrated in the drawings. The invention is capable of other embodiments and of being practiced and carried out in various ways. It is to be understood that the terminology employed herein is for the purpose of the description and should not be regarded as limiting.

What I claim is:

1. A Huber needle safety system comprising:
   a base wherein said base includes a base bottom at one distal end, a base tower, and a base top at a proximal end, wherein the base tower and the base top are hollow and include a base tower cut out and a base top cut out and wherein the base bottom is configured to matingly engage with a subcutaneous port;
   a collar, wherein the collar is configured to matingly engage with the base tower and includes a collar cut out for alignment with the base tower cut out and said base top cut out;
   and a needle assembly wherein the needle assembly includes a hollow needle housing with a top surface and bottom surface, and a needle that is disposed within the hollow needle housing, wherein the needle housing includes a cap, a depressor handle, and a retaining lip wherein the retaining lip is retained within the base tower such that the needle is fully disposed within the base tower prior to deployment into said subcutaneous port
   and wherein, upon proper alignment of the base tower cut out, the base top cut out, and the collar cut out, the depressor handle of the needle assembly is configured to be depressed upon deployment of the needle into the subcutaneous port.

2. The Huber needle safety system of claim 1 in which said bottom surface of said housing of said needle assembly includes a needle aperture through which the tip of said needle passes.

3. The Huber needle safety system of claim 1 in which the cap of the needle assembly housing is annular in cross section.

4. The Huber needle safety system of claim 3 in which the retaining lip of the needle assembly housing is annular in cross section and has a diameter greater than the diameter of the needle assembly housing needle assembly cap.

5. The Huber needle safety system of claim 1 in which said base bottom is annular in cross section and includes a base bottom upper surface, a base bottom lower surface opposite thereto, and a base bottom side wall substantially perpendicular to the base bottom upper surface and the base bottom lower surface.

6. The Huber needle safety system of claim 5 wherein said base bottom lower surface includes a recess for matingly engaging a port.

7. The Huber needle safety system of claim 5 wherein said base bottom includes ventilation holes wherein said ventilation holes pass through from said base bottom upper surface to said base bottom lower surface.

8. The Huber needle safety system of claim 1 wherein said base tower extends substantially perpendicularly from said base bottom and wherein said base tower is annular in cross section and includes a base tower inner wall and a base tower outer wall.

9. The Huber needle safety system of claim 8 wherein said base top extends outwardly past said base tower outer wall and over said base tower inner wall.

10. The Huber needle safety system of claim 1 wherein the base tower cut out is arranged along the longitudinal axis of the base tower and extends from the base bottom to the base top.

11. The Huber needle safety system of claim 1 wherein said base top is substantially C-shaped.

12. The Huber needle safety system of claim 1 wherein the collar is substantially C-shaped in cross section and includes a collar top surface, a collar bottom surface opposite thereto, a collar outer side wall and a collar inner side wall opposite the collar outer side wall wherein the collar outside wall is substantially perpendicular to the collar bottom surface and the collar to surface.

13. The Huber needle safety system of claim 12 wherein said collar outer wall includes a plurality of grips, wherein said grips are disposed at regular intervals along said collar outer side wall.

\* \* \* \* \*